United States Patent [19]

Imaizumi et al.

[11] Patent Number: 4,640,123
[45] Date of Patent: Feb. 3, 1987

[54] LEAK DETECTING DEVICE

[75] Inventors: Haruo Imaizumi, Nishi-Asuma; Satoru Kobayashi, Hitaka, both of Japan

[73] Assignee: Junkosha Company, Ltd., Tokyo, Japan

[21] Appl. No.: 768,456

[22] Filed: Aug. 22, 1985

[30] Foreign Application Priority Data

Aug. 29, 1984 [JP] Japan ................................. 59-181262

[51] Int. Cl.$^4$ ............................................ G01N 27/00
[52] U.S. Cl. ................................................. 73/61.1 R
[58] Field of Search ..................... 73/61.1 R, 61 R, 53; 134/184

[56] References Cited

U.S. PATENT DOCUMENTS 3,762,214 10/1973 Bogusz ................................. 73/61 R Primary Examiner—Jerry W. Myracle
Assistant Examiner—Joseph W. Roskos
Attorney, Agent, or Firm—Mortenson & Uebler

[57] ABSTRACT

In a device for detecting oil leaks and the like on a surface of water such as a moat around an oil storage tank, a vibrator is placed which substantially eliminates extraneous matter attaching to or depositing on the sensor and thereby enhances the conditions for leak detection.

3 Claims, 4 Drawing Figures

LEAK DETECTING DEVICE

BACKGROUND OF THE INVENTION

The present invention relates to an improvement in a device for detecting the leakage of vapors of liquid hydrocarbons such as petroleum, gasoline or heavy oil, a variety of organic solvents such as carbon tetrachloride or methylethylketone (MEK), or a variety of liquids having a high vapor pressure such as MEK, gasoline or ammonia, into or onto the water which, for example, surrounds an oil storage tank.

The present applicant has previously proposed a liquid detecting element as disclosed in Japanese Patent Laid Open Publication No. 53-145697. In that case, the liquid detecting element has a drawback in that its detecting sensitivity is extremely decreased with the passage of days in situations in which it is positioned in water to detect the leakage of liquid into or onto the water. This decrease is caused by the adhesion to or growth onto the device of extraneous matter in the water contents, and these extraneous substances frequently have to be removed from the surface of the detecting element which takes a considerable amount of time for maintenance and must be undertaken with prior art devices so that the original detecting sensitivity may be recovered.

In view of the foregoing, it is an object of the present invention to provide a leakage detecting device for which the maintenance of removal of the extraneous substances in water is substantially eliminated.

SUMMARY OF THE INVENTION

A leak detecting device is provided comprising a detecting element contained in a suitable housing and submerged at least partially in water for detecting the leakage of a substance different from water, and a vibrator disposed in the vicinity of the detecting element for applying periodic vibrations to said detecting element at a suitable frequency. The detecting element can be arranged on the outer surface of a column-shaped vibrator and held in a support system which is supported by the vibrator, or the vibrator may be plate-shaped and laminated onto one side of a plate-shaped detecting element, wherein the vibrator may include a pair of plate-shaped electrodes and a vibrating element sandwiched between the pair of electrodes, this entire assembly being laminated onto one side of the detecting element.

DETAILED DESCRIPTION OF THE INVENTION AND PREFERRED EMBODIMENTS WITH REFERENCE TO THE DRAWINGS

In a device for detecting oil leaks and the like on a surface of water such as a moat around an oil storage tank, a vibrator is placed which substantially eliminates extraneous matter attaching to or depositing on the sensor and thereby enhances the conditions for leak detection.

In order to eliminate problems associated with prior art devices, the present invention, a leakage detecting device, is constructed comprising a detecting element submerged at least partially in water for detecting leakage in or on the water of a substance such as oil different from the water, and having a vibrator disposed in the vicinity of the detecting element for applying periodic vibrations to the detecting element at a desired frequency.

In a preferred construction, the detecting element is advantageously arranged on the outer circumference of a column-shaped vibrator and may be held in a support system which is supported on the vibrator. According to an alternate embodiment of the present invention, moreover, a plate-shaped vibrator may be laminated on one side of a flat detecting element.

According to the present invention, the vibrator is disposed in the vicinity of the detecting element which is submerged at least partially in the water for detecting the leakage of a substance different from the water. As a result, the extraneous substances having adhered to the surface of the detecting element are vibrated and scattered into the water by vibrating the vibrator at a desired frequency so that the detecting element has its surface cleaned to restore its sensitivity.

The relative positions of the detecting element and the vibrator are preferably set such that the vibrations of the vibrator are efficiently transmitted to the detecting element. For example, it is effective either to form the vibrator into a columnar shape so that the detecting element is disposed on the outer circumference of the vibrator or affix the detecting element in a support system which is supported by the vibrator. If the vibrator is formed into a plate-like shape and is laminated on one side of a flat detecting element, the vibrations can be applied suitably to the detecting element so that the object of the invention can be economically achieved with little required vibratory energy.

Figure 1:
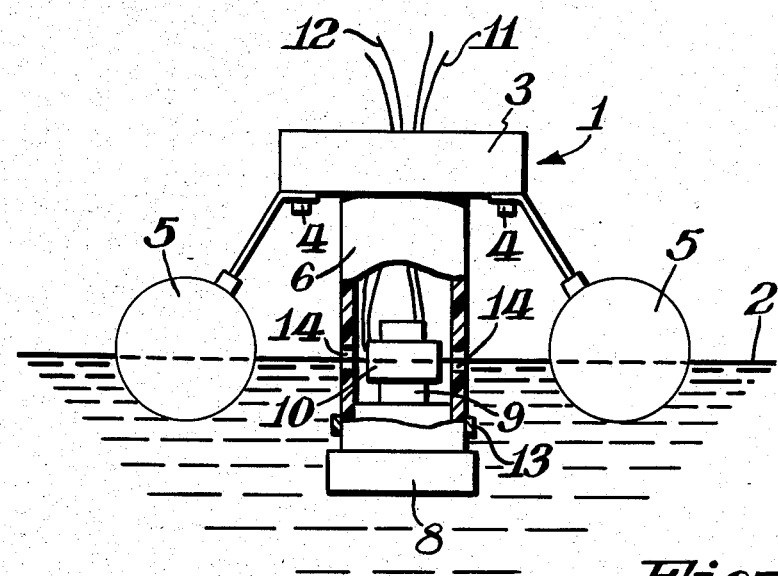
FIG. 1 is a side elevation, partly in cross-section, showing a leakage detecting device according to the present invention.

FIG. 1 is a side elevation, partly in cross-section, showing a leak detecting device of the floating type according to the present invention.

This leak detecting device 1 is used to detect the leakage of oil or the like onto a water surface 2 and floats on the water surface 2 by means of floats 5 which are affixed to support flange 3 by bolts 4 or the like. To the lower face of the support flange 3 there is affixed support cylinder 6 having a lower end, to which is attached a stabilizing counter weight 8.

On the upper face of weight 8 is mounted a column-shaped vibrator 9 to the outer surface of which is attached a detecting element 10. The vibrator 9 and the detecting element 10 have their respective feeder lead wires 11 and lead wires 12 extending to an external power source (not shown). Reference numeral 13 indicates a fixing member for attaching the weight 8 to the lower end portion of the support cylinder 6, and numeral 14 indicates openings which are positioned at a level corresponding to the water surface of the support cylinder 6 through which the water flows.

In the leak detecting device 1 thus constructed, the detecting element 10 has at least a portion submerged in the water. Its surface is in contact with the extraneous substances contained in or floating on the water, and these substances grow and deteriorate with the passage of time, e.g. days. As a result, the sensitivity of the detecting element drastically decreases after about twenty days or so. Since the vibrator 9 is disposed in the vicinity of the detecting element 10 in accordance with the present invention, however, it is energized to vibrate by supplying power to the lead wires 11 at intervals of the twenty days or shorter. As a result, the detecting element 10 has its surface cleared of the extraneous substances so that it is maintained in good operating state, and it is generally unnecessary to periodically clean the surface of the detecting element 10 of the extraneous substances.

Figure 2:
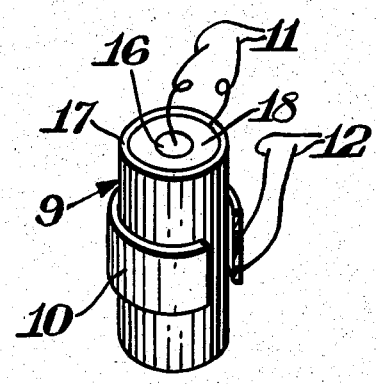
FIG. 2 is a perspective view showing the column-shaped vibrator of the device of FIG. 1.

FIG. 2 is a perspective view showing the cylindrical vibrator 9 which is used in the embodiment of FIG. 1. This vibrator 9 is formed into a column shape by sandwiching a charge vibrator 18 such as a piezoelectric crystal between a central conductor 16 and a circumferential conductor 17. The detecting element 10 is attached to the surface of the vibrator 9 thus constructed.

Figure 3:
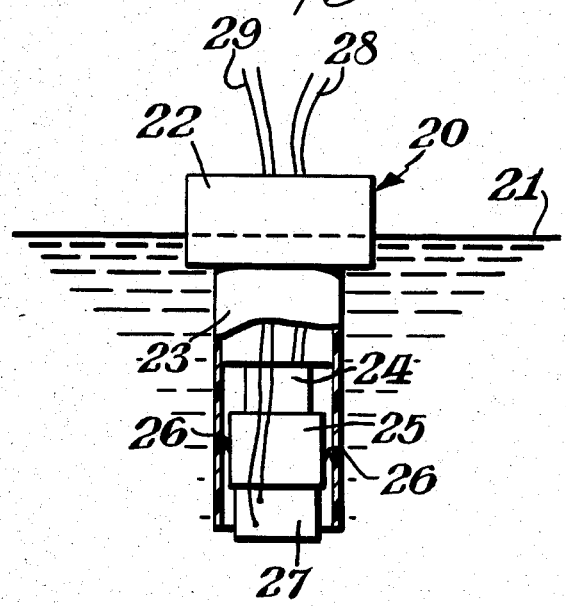
FIG. 3 is a side elevation, partly in cross-section, showing a leakage detecting device according to another embodiment of the present invention.

FIG. 3 is a side elevation, partly in cross-section, showing a leak detecting device 20 of the submerged type according to the present invention. This leakage detecting device 20 is used to detect either a leaking gas which floats up to the water surface 21 or a leaking liquid having a lower specific gravity than that of the water.

The leakage detecting device 20 according to this embodiment is equipped at its top with float 22 having a lower side, to which is affixed a support cylinder 23. A vibrator 24 is attached to the intermediate portion of the support cylinder 23.

To the lower end portion of vibrator 24 there is attached a vibratory support system 25, which is guided into the support cylinder 23 through a compressible elastic member 26. Detecting element 27 is affixed to the lower end portion of vibratory support system 25. The vibrator 24 has its charging lead wires 28 led to external power supply (not shown) through float 22.

In this embodiment, if the vibrator 24 is operated to vibrate by supplying power intermittently to lead wires 28, the resultant vibratory energy is transmitted through the vibratory support system 25 to the detecting element 27. If the support system 25 is made to resonate, the vibratory energy is amplified so that the amplified vibratory energy can be applied to the detecting element 27. If the vibrations are thus intermittently applied to the detecting element 27, the detecting element 27 has its surface cleared of extraneous substances so that its surface is maintained in a good operating state. In this case, the work of removing the extraneous substances from the surfaces of the detecting element 27 is substantially eliminated.

Figure 4:
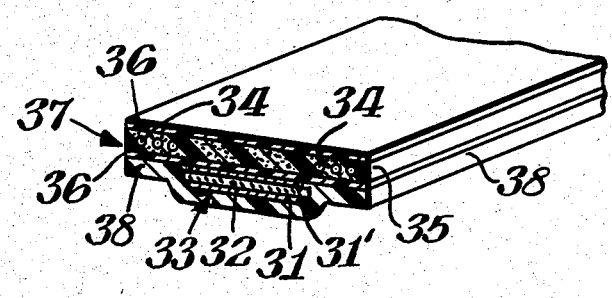
FIG. 4 is a transverse perspective view, partly in cross-section, showing an integrated, flat-plate-like laminate of the detecting element and the vibrator.

FIG. 4 shows an embodiment in which a plate-shaped vibrator such as a piezoelectric crystal plate and detecting element are laminated integrally, one on the other. As shown, a plate-shaped vibrator 33, which is constructed of a plate-shaped charge vibrator 32 sandwiched between a pair of plate-shaped electrodes 31 and 31', is laminated integrally by means of resin cover 38 on the lower face of a detecting layer element 37 which is arranged with spaced conductors 34 within a layer 35 of a conductive resin of polytetrafluoroethylene, and covered with insulating resin layer 36.

Thus, owing to the integrated structure in which the plate-shaped vibrator 33 and the detecting element 37 are laminated, removal of the extraneous substances can be advantageously attained using a relatively small output of vibrator 33. Another advantage obtained is that the device is small in size.

As described above, according to the present invention, a leak detecting device is provided comprising a detecting element submerged at least partially in water for detecting leakage of a substance different from water, and a vibrator is disposed in the vicinity of the detecting element of applying vibrations to the detecting element at a desirable frequency. As a result, the vibrations can be applied either continuously or intermittently to the detecting element so that the surface of the detecting element is cleared of or prevented from the attack of extraneous substances. This makes it substantially unnecessary to clear the surface of the detecting element of the extraneous substances, and little maintenance is required in an economical system.

In the present invention, moreover, the vibratory energy required can be reduced either by sandwiching the vibratory support system between the vibrator and the detecting element or by forming the vibrator into a plate-like shape and laminating it integrally onto a plate-shaped detecting element.

The present invention is not limited to the foregoing embodiments, but its effects can be achieved by modifications within the scope of the concept of the present invention known to those skilled in the art, such as by changing the shapes of the vibrator and the detecting element or by changing the relative positions of the vibrator and the detecting element.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. A leak detecting device comprising a detecting element contained in a suitable housing and submerged at least partially in water for detecting the leakage of a substance different from said water, and a vibrator disposed in the vicinity of said detecting element for applying periodic vibrations to said detecting element at a suitable frequency, wherein said detecting element is arranged on the outer surface of a column-shaped vibrator.

2. A leak detecting device comprising a detecting element contained in a suitable housing and submerged at least partially in water for detecting the leakage of a substance different from said water, and a vibrator disposed in the vicinity of said detecting element for applying periodic vibrations to said detecting element at a suitable frequency, wherein said vibrator is plate-shaped and is laminated on one side of said detecting element.

3. A leak detecting device as set forth in claim 2, wherein said vibrator includes a pair of plate-shaped electrodes and a vibrating element sandwiched between said pair of electrodes, this entire assembly being laminated onto one side of said detecting element.

* * * * *